United States Patent [19]

Costello

[11] Patent Number: 5,137,722
[45] Date of Patent: Aug. 11, 1992

[54] EXTRACT AND PHARMACEUTICAL COMPOSITION FOR TREATMENT OF CALCIUM OXALATE STONE DISEASE

[75] Inventor: Jeremiah Costello, Wexford, Pa.

[73] Assignee: Allegheny-Singer Research Institute, Pittsburgh, Pa.

[21] Appl. No.: 641,763

[22] Filed: Jan. 16, 1991

[51] Int. Cl.$^5$ .............................................. A61K 35/78
[52] U.S. Cl. ................... 424/195.1; 514/891
[58] Field of Search ................ 424/195.1; 514/891

[56] References Cited

U.S. PATENT DOCUMENTS

| | | | |
|---|---|---|---|
| 4,264,463 | 4/1981 | Kotake et al. | 252/87 |
| 4,336,397 | 6/1982 | Cragoe, Jr. et al. | 560/51 |
| 4,337,258 | 6/1982 | Rooney et al. | 514/277 |
| 4,399,003 | 8/1983 | Sarig et al. | 204/1 |
| 4,423,063 | 12/1983 | Rooney et al. | 514/450 |
| 4,428,956 | 1/1984 | Cragoe, Jr. et al. | 514/391 |
| 4,431,652 | 2/1984 | Cragoe, Jr. et al. | 514/365 |
| 4,431,660 | 2/1984 | Cragoe, Jr. et al. | 514/425 |
| 4,597,952 | 7/1986 | Fabre et al. | 423/122 |
| 4,689,322 | 8/1987 | Kulbe et al. | 514/54 |
| 4,804,476 | 2/1989 | Sinkovitz et al. | 210/697 |

OTHER PUBLICATIONS

Walenga et al., Seminars in Thrombosis and Hemostasis, vol. 17, Supplement 2, pp. 137–142 (1991).
Strohmaier et al, "Excretion of glycosaminoglycans (GAG) . . . D-glucosamine", pp. 205–210.
Martelli et al, "Multisulphated dermatan as a GAG . . . calcium oxalate stone formation", pp. 197–203.
Danielson et al, "Glycosaminoglycans as inhibitors . . . clinical practice", pp. 193–195.
"Inhibitors of Crystallization . . . Clinical Application", Proc. of the Int'l. Mtg. held in Bologna, Sep. 7–9 (1987), pp. 271–282.
Ashan et al, Journal of Ethnopharmacology, vol. 26, pp. 249–254 (1989).
Jianzhong, Journal of Traditional Chinese Medicine, 2(3), pp. 187–194 (1982).
Fellstrom et al, Clinical Science, vol. 71, pp. 61–64 (1986).
Brown et al, Urolithiasis and Related Clinical Research, pp. 891–894 (1985).
Schneider, "Medical Plant Agents . . . Recurrent Urolithiasis", p. 863 (1989).

*Primary Examiner*—John W. Rollins
*Attorney, Agent, or Firm*—Birch, Stewart, Kolasch & Birch

[57] ABSTRACT

An extract for the treatment of calcium oxalate kidney stone disease which can be extracted and purified from leaves of the plant *Eriobotrya japonica* is disclosed. The extract has the following characteristics: inhibits calcium oxalate crystal growth in vitro, inhibits renal calcium oxalate crystal deposition in rats which are fed ethylene glycol, causes rats which are fed ethylene glycol and said extract to excrete less oxalate in their urine as compared to rats which are fed ethylene glycol without said extract, shows little or no loss in activity when exposed to an aqueous solution of pH 1.5 for 14 hours, shows increased activity when exposed to an aqueous solution of pH 12.7 for 15 hours, is polyanionic, is stable when heated in an aqueous solution (at pH of extract) at 98° C. for 3 hours, water-soluble, insoluble in heptane, hexane, chloroform/methanol mix, diethyl ether, and ethanol/aqueous mix, binds to DEAE-A-25 Sephadex at pH 8.6 and is eluted from the DEAE-A-25 Sephadex with 2 M NaCl. The present invention is also directed to a method for the treatment of calcium oxalate stone disease wherein the extract is administered, preferably for a prolonged period of time, to a patient suffering from or prone to calcium oxalate stone disease.

19 Claims, No Drawings

EXTRACT AND PHARMACEUTICAL COMPOSITION FOR TREATMENT OF CALCIUM OXALATE STONE DISEASE

BACKGROUND OF THE INVENTION

1. Technical Field

The present invention relates to the treatment of calcium oxalate stone disease.

2. Description of Background Art

Calcium oxalate is the most common constituent of urinary calculi and relatively large crystals of this salt are frequently found in freshly voided urine from patients with recurrent calcium-containing stones. The rate of crystal growth and aggregation of calcium oxalate will determine whether or not a particle large enough to be trapped at some narrow point in the urinary tract can be formed within the transit time of urine through the urinary system. The chance of a particle being trapped depends partly on the size of the particle. The rate of crystal growth may determine to a large extent the subsequent rate of growth of this nidus into a stone. It is well known that several urinary constituents (e.g., pyrophosphate, glycosaminoglycans, citrate) can inhibit the rate of growth and/or aggregation of seed crystals of calcium oxalate in vitro.

Considerable research effort has been and is being expended in an attempt to identify or synthesize compounds that act as inhibitors of calcium oxalate crystal growth and which could be used for treatment of patients suffering from recurrent kidney stone disease. Hydrochlorothiazide, sodium potassium phosphate, and potassium citrate are drugs available for the treatment of calcium oxalate stone disease and reported to reduce its recurrence. These and other drugs available have not been shown to dissolve or remove kidney stones/fragments. The development of drugs more effective in preventing calcium oxalate stone formation and to dissolve kidney stones/fragments is still needed. Since recurrence of stone disease is believed to be largely due to such remnant stone fragments in the kidney, following lithotripsy or other stone removal procedures, their dissolution could dramatically reduce recurrence rates.

SUMMARY OF THE INVENTION

Accordingly, it is an object of the present invention to provide an extract for treatment of calcium oxalate stone disease which is effective in practical use. More specifically, it is an object of the present invention to provide an extract for treatment of calcium oxalate stone disease which exhibits one or more of the following desirable properties (1) it is non-toxic, i.e., safe for human intake, (2) it is absorbed in the gut when taken by oral ingestion, (3) it is excreted by patients in urine, (4) it prevents the formation of and/or dissolves calcium oxalate kidney stones and (5) it does not adversely affect bones of patients treated with the extract.

The above objects are accomplished by providing a purified extract which possesses one or more of the following properties: inhibits calcium oxalate crystal growth in vitro: inhibits renal calcium oxalate crystal deposition in rats which are fed 1% ethylene glycol; causes rats which are fed ethylene glycol and the extract to excrete less oxalate in their urine as compared to rats which are fed ethylene glycol without the extract; retains activity when exposed to an aqueous solution of pH 1.5 for 14 hours; retains or shows increased activity when exposed to an aqueous solution of pH 12.7 for 15<hours,; is stable when heated in a neutral aqueous solution (at pH of extract) at 98° C. for at least 3 hours; is water soluble; is insoluble in heptane, hexane, diethyl ether and chloroform/methanol mix (1:1); is precipitated out of solution by absolute ethanol, ethanol:aqueous extract (2.5:1 by volume); binds to DEAE-A-25 Sephadex at pH 8.6; is eluted from the DEAE-A-25 Sephadex with 2M NaCl, which is evidence that it is anionic; binds to calcium oxalate crystals; has an isoelectric point (pI) of $2.7 \pm 0.5$ (mean$\pm$SD).

The present invention is also directed to a modified extract which can be formed by treating the extract of the present invention at a basic pH such as a pH of 12 or more to thereby produce a modified extract which has increased inhibitory activity against calcium oxalate crystal growth as compared with the extract which has not been treated with base. Based on in vitro studies, this modified extract appears to have the same properties as the untreated extract except that it has a higher activity as discussed above. The modified extract is preferably used in a purified form.

The extract of the present invention can be prepared by a variety of established methods for both extraction and purification. One such method is the one described in the present application. In another approach, for example, the extract of the present invention can be prepared by obtaining the extract from cells of the plant *Eriobotrya japonica*, purifying the extract by contacting the extract with an anion exchange material which selectively binds negatively charged materials, and recovering the extract from the anion exchange material.

The present invention is also directed to a pharmaceutical composition suitable for the treatment of calcium oxalate stone disease which contains an effective amount of the above-described extract with or without an appropriate pharmaceutically acceptable carrier therefor and a method for treating calcium oxalate stone disease which comprises administering to a subject an effective amount of the above-described extract or composition.

DESCRIPTION OF THE PREFERRED EMBODIMENT

The extract of the present invention is preferably present in a purified form when administered to a patient. When the extract is extracted from plant leaves, it is desirable to separate soluble extract from (residual) particulate matter by appropriate means (filtration, centrifugation, or other separation techniques, etc.). The utility of the extract as a therapeutic agent is enhanced by greater purification. Greater dosages may be necessary for less pure forms of the extract.

The extract of the present invention is preferably substantially free from heavy metals, contaminating plant materials, contaminating microorganisms, oxalic acid or precursors of oxalic acid or any other contaminants which would normally be present in a crude preparation derived from plant material.

After purification, the extract should have a purity level of at least 50,000, preferably at least 150,000 and more preferably at least 175,000 Units of activity per gram of solid matter. The extract prepared to date has a purity level of between about 50,000 and about 250,000, preferably between about 150,000 and about 250,000, and most preferably between about 175,000 and about 200,000 Units of activity per gram of solid matter, i.e., matter remaining after evaporation of all liquids. As used in this application, the term "units" is defined as follows. One unit of inhibitory activity is defined as the quantity of extract that causes 50% inhibition of calcium oxalate crystal growth in the assay system described.

Zero inhibition is where the amount of radioactivity lost from solution, during the assay, is equivalent to or more than that lost from the Reference sample.

One hundred percent inhibition is where there is no loss of radioactivity from solution during the crystal growth assay. To Calculate % inhibition of any sample:
1. Determine dpm (disintegrations per minute) lost from reference sample (Reference Sample has 0.15 M NaCl in place of sample) = Total dpm added/100 µl - dpm/100 µl in solution at end of the assay
2. Determine as in (1) dpm lost from the analytical sample
3. dpm lost (reference sample) - dpm lost (Analytical Sample)
4. $\frac{\text{Result of (3) dpm}}{\text{dpm lost from reference sample}} \times 100 = \%$ inhibition 5. Units of activity in analytical sample: = % inhibition ÷ 50 = Units of activity

EXAMPLE

Calculation of % inhibition and inhibitory activity of extract #60, Table 1.

1. $11,252 - 5,434 = 5,818$ dpm
2. $11,252 - 9,732 = 1,520$ dpm
3. $5,818 - 1,520 = 4,298$ dpm
4. $\frac{4,298 \times 100}{5,818} = 73.9\%$ inhibition
5. $\frac{73.9}{50} = 1.48$ Units of inhibitory activity/10 µl of Extract #60

The following abbreviations, wherever they are used in this application, shall have the meanings ascribed thereto unless some other meaning is clearly required by the context in which such term is used: AA (Atomic Absorption), BUN (Blood Urea Nitrogen), Ci (Curie), dpm (disintegrations per minute), EDTA (ethylenediaminetetraacetic acid), EG (ethylene glycol), EGTA (ethylene glycol-bis (betaaminoethyl ether)-N,N,N',N',-tetraacetic acid),g (gravity), gr (gram(s)), h (hour(s)), kg (Kilogram(s)), M (molar), mg (milligram(s)), ml (milliliter(s)), N (normality), NS (not significant), P-P (pyrophosphate), and rpm (revolutions per minute), U (units), V (volume), W (weight), pI (isoelectric point).

The extract of the present invention can be used for the treatment and/or prevention of calcium oxalate stone disease by administering an effective amount of the extract to a subject. For laboratory experiments, laboratory mammals such as rats, mice, monkeys, as well as other mammals can be used. However, the ultimately desired use is to treat human patients who suffer from calcium oxalate stone disease.

It is contemplated that the extract will be formulated into a pharmaceutical composition comprising an effective amount of the extract with or without a pharmaceutically acceptable carrier. The pharmaceutically acceptable carrier may be any carrier which is non-toxic, i.e., safe for human intake, and which is compatible with the extract and the desired route of administration.

In a particular embodiment of the invention, the therapeutic or pharmaceutical composition comprises the extract in an effective unit dosage form. As used herein, the term "effective unit dosage" or "effective unit dose" means a predetermined amount of the extract sufficient to be effective for dissolution of calcium oxalate kidney stones in vivo or effective to prevent or reduce the degree of formation of kidney stones in vivo. Pharmaceutically acceptable carriers are materials useful for the purpose of administering the extract, which are preferably non-toxic, i.e., safe for human intake, and may be solid, liquid or gaseous material, which are otherwise inert and medically acceptable and are compatible with the active ingredient. The pharmaceutically acceptable carrier may be a carrier of a type which has been or would be approved by the Food and Drug Administration for administration to human subjects which have experienced calcium oxalate kidney stones. The pharmaceutical compositions may contain other active ingredients such as magnesium, Vitamin $B_6$ or potassium citrate. The pharmaceutical composition may also contain other active ingredients which are effective against calcium oxalate kidney stone disease.

The pharmaceutical compositions may be administered orally or parenterally, including by injection, subcutaneously or used as a suppository or pessary. The only limitation on the route of administration is that the compound should reach the kidneys in an amount effective to treat kidney stone disease. It is also possible that it may be desirable for the extract to reach the urinary tract or bladder of the patient being treated.

The compositions may contain 5,000 to 30,000, more preferably 10,000 to 20,000 Units of the extract per unit dosage. Typically, the extract will be present in an amount of 0.1 to 90 percent by weight of the pharmaceutical composition, preferably 0.5 to 50 percent by weight of the pharmaceutical composition.

At the present time, oral administration is preferred since the extract appears to be absorbed through the gut and transported to and excreted by the kidneys. For oral administration, fine powders or granules may contain diluting, dispersing and/or surface active agents, and may be presented in a draught, in water or in a syrup; in capsules in the dry state or in a non-aqueous solution or suspension, wherein suspending agents may be included; in tablets, wherein binders and lubricants may be included; or in a solution or suspension in water or other liquid or a syrup. Where desirable or necessary, flavoring, preserving, suspending, thickening or emulsifying agents may be included. Tablets and granules are preferred and these may be coated.

For oral administration, the daily dosage as employed for adult human treatment may range from about 5,000 to 30,000 Units, preferably about 10,000 to 20,000 Units, which may be administered in 1 to 5 daily doses, for example, depending on the route of administration and the condition of the patient. When the composition comprises dosage units, each dosage unit may contain about 1,000 to 20,000 Units of active ingredient, preferably about 5,000 to 10,000 Units. Dosages for human therapy will be established by standard techniques through the experience gained in clinical trials. Initial estimates are based on the following assumptions.

In order to prevent renal stone formation in rats (300 gr weight) during ethylene glycol ingestion, a daily dose of 487 Units (unpurified extract) was administered. To treat a 70 kg man with recurrent calcium oxalate stone disease, the following calculated dose units, based on rat studies, may be appropriate. Rats were given 1623 Units/kg weight/day. In extrapolating from Units/kg in the rat to Units/kg in man for drug concentrations, a correction factor of 1/7 has been applied (Goldin, A. et al, Quantitative and qualitative prediction of toxicity from animals to humans. In: Tagnon H. J., Stagnet M. J. (eds.), Controversies in Cancer, New York: Masson Publishing USA, Inc., pp. 83–104 (1978)), resulting in 232 Units/kg/day for man (1623×1/7). Using this treatment dose, a man of 70 kg should receive 16,240 Units of inhibitor/day. When the purified extract (inhibitor) contains 183,871 Units/gr, then a daily dose of 88 mg would provide the appropriate quantity of inhibitor.

For buccal administration the compositions may take the form of tablets, gum, syrups as well as other liquid forms, lozenges formulated in a conventional manner.

The extract of the invention may also be formulated for injection and may be presented in unit dose forms in ampules or in multi-dose containers with or without an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile physiological saline, before use.

The compound preferably will be administered to a patient as soon as a diagnosis of stone disease has been made and more preferably after a determination that a patient suffers from recurrent kidney stones containing calcium oxalate. The treatment preferably will continue on a daily basis for at least five days, more preferably at least two weeks and even more preferably for at least one month. The compound may be administered at least three times a week for at least three months to prevent or reduce recurrence of stone disease It is also possible that if recurrence of calcium oxalate kidney stones is or has been a significant problem for a particular patient, treatment may continue indefinitely, e.g., it may continue for the rest of a patient's life. It is anticipated that if the compound of the present invention is administered to patients for prolonged periods of time, the recurrence of kidney stones can be prevented or minimized.

It is also possible that other forms of treatment can be used in conjunction with administration of the compound of the present invention, i.e., ultrasound treatment to break up the stones can be utilized on a patient who has been treated with the compound of the present invention.

The compound could be used to treat the great majority of patients suffering from recurrent stone disease, since over 75% of all renal stones contain calcium oxalate. For example, the compound may be useful to prevent formation of stones by preventing or inhibiting nucleation, growth and/or aggregation of crystals. It could also be used to treat these patients following extracorporeal shockwave lithotripsy to help ensure passage in the urine of shattered stone particles and renal crystal deposits. The compound may also be effective in treating patients with primary hyperoxaluria (a genetic disease resulting in massive over-production of oxalic acid) many of whom suffer total loss of renal function in the early years of life. The compound has potential use in dissolving recurrent renal stones in patients with a history of calcium oxalate stone disease. This could result in less frequent use of the lithotripter and other techniques now used to remove kidney stones The compound may have use in treating patients post renal transplantation in order to prevent calcium oxalate deposition in the renal graft since many of these patients have substantial body stores of calcium oxalate following long-term dialysis. Finally, it is possible that the compound could be used to treat patients suffering from systemic oxalosis, i.e., deposition of calcium oxalate crystals in many tissues of the body. The stones being treated (or the formation of which is to be prevented) may be present in the kidney, bladder and/or urinary tract.

Although at present isolation of the extract from the leaves of *Eriobotrya japonica* plants is the most practical method for obtaining the compound, the present invention also contemplates obtaining the extract from other sources such as other plants which may contain recoverable amounts of the extract. It is also possible that the extract could be obtained by culturing plant cells, such as *Eriobotrya japonica* cells, in vitro and extracting the active ingredient from the cells or recovering the active ingredient from the cell culture medium. The present invention also contemplates the use of synthetic compounds having the above-described characteristics. Presumably, such synthetic compounds could be synthesized after the chemical structure of the extract of the present invention has been elucidated.

As used herein, the term "extract" means the active ingredients isolated from leaves or other parts of *Eriobotrya japonica* or other natural sources including but not limited to all varieties, species, hybrids or genera of the plant regardless of the exact structure of the active ingredients, form or method of preparation or method of isolation. The term "extract" is also intended to encompass salts, complexes and/or derivatives of the extract which possess the above-described biological characteristics or therapeutic indication. The term "extract" is also intended to cover synthetically or biologically produced active ingredients with the same or similar characteristics yielding the same or similar biological effects.

The Examples that follow describe extraction of *Eriobotrya japonica* plant leaves and the effect of the extract on: i) inhibition of calcium oxalate crystal growth in vitro, ii) inhibition of stone formation and crystal deposition in vivo in a rat model, and iii) dissolution of renal stones in vivo in a rat model.

EXAMPLE 1

*Eriobotrya japonica* plant leaves are removed from a tree and are stored at -20° C. the day they are removed from the tree or extracted the same day. Before extraction, fresh or frozen leaves are gently hand-washed in water at 35° C. to remove surface dirt. Aliquots of the leaves are then homogenized in distilled water with a food mincer for two to four minutes at room temperature. The entire homogenate (containing 150 g of leaves) is combined in a conical Pyrex flask and made up to 1300 ml with further addition of distilled water. The homogenate is brought to a boil and allowed to simmer for 4.5±1.5 h. The temperature of the solution during the extraction is 90°–105° C. The extract is allowed to and the solution poured through a funnel containing a stainless steel wire mesh which retains the leaf particles. A precipitate which settles at the bottom of the flask is discarded and only the clear supernatant retained The volume of the extract is brought to 1300 ml by addition of water to compensate for losses by evaporation during extraction. The extract is stored in the form of a frozen liquid at −20° C. or lower. Various batches of the extract in the form of a frozen solution have been designated N-1 N-2 N-3 #-60 etc. These extracts were prepared at different times from different *Eriobotrya japonica* plants. Instead of bringing the volume to 1300 ml, the extract can be lyophilized to prepare a powder.

EXAMPLE 2

To determine the effect of the extract on calcium oxalate crystal growth, a modification of the method of Ligabue et al, Clin. Chim. Acta, 98, 39 (1979) was used. The principle of the assay is based on the loss of oxalate, over time, from a metastable solution of calcium oxalate following addition of calcium oxalate crystals. The loss of oxalate from solution represents crystal growth of calcium oxalate. The inhibitory effect of an extract is determined by adding the extract to the metastable solution and comparing the rate of crystal growth to that in its absence.

The inhibitory activity of the extract as well as the inhibitory activity of citrate and pyrophosphate, two compounds known to inhibit calcium oxalate crystal growth under conditions described above, was determined.

The metastable solution used in this experiment contained the following:

| | |
|---|---|
| NaCl | 0.15 M |
| $CaCl_2$ | 1.0 mM |
| $Na_2C_2O_4$ (sodium oxalate) | 0.2 mM |
| Na cacodylate | 5.0 mM |

The solution, 200 ml, was brought to 37° C. and filtered through a millipore filter (0.45 μm). To the filtrate, $^{14}$C-oxalate (3.4 m Ci/mmol) was added to give approximately 10,000 disintegrations per minute (dpm)/100μl [100 μl of $^{14}$C-oxalate (50 μ Ci/ml)/100 ml filtrate]. The pH of the solution was adjusted to 6.0. A 100 mM solution of citrate and a 1.2 mM solution of pyrophosphate were prepared on the day of the assay. Aliquots, 50 μl and 10 μl, respectively, of these solutions were analyzed for inhibitory activity. Aliquots, 10 μl, of two extract preparations, which had been stored at −20° C, were analyzed.

A stock suspension of seed crystals, 200 mg of calcium oxalate monohydrate crystals in 200 ml of 0.15 M NaCl, was prepared and incubated with magnetic stirring for a minimum of 48 hours (h) at 37° C. before using.

Test tubes were set up containing 5 ml of the metastable - $^{14}$C-oxalate solution at 37° C. Aliquots of samples for analysis, 5-50 μl, were added to appropriate tubes, followed by 200 μl of seed crystal suspension. Tubes were capped and continuously mixed during incubation, for 90 minutes at 37° C. Tubes were then centrifuged (5 min, 1500 rpm) and aliquots (100 μl) removed from the supernatant for radioactive counting in 5 ml of Biofluor and counted on a Packard liquid scintillation counter. All samples were run in duplicate, while triplicate analysis of the reference tubes (0.15 M NaCl in place of inhibitor) and "total tubes" (no crystals added) was run. The results of this study are shown in Table 1. Results are expressed as percentage loss of $^{14}$C-oxalate from solution.

TABLE 1

The Effect of Two Extract Preparations, Pyrophosphate (P~P), and Citrate on Calcium Oxalate Crystal Growth In Vitro.

| SAMPLE | dpm REMAINING | % LOSS (GROWTH) |
|---|---|---|
| *Total dpm | 11,252 | — |
| *Reference (0.15M NaCl) (50 μl) | 5,434 | 51.7 |
| Extract #N-1, (10 μl) | 8,403 | 25.3 |
| #60, (10 μl) | 9,732 | 13.5 |
| P~P (1.25 mM), 10 μl | 8,619 | 23.4 |
| Citrate (100 mM), 50 μl | 8,829 | 21.5 |

*Mean of triplicate determinations. All other samples were assayed in duplicate.

The reference sample showed 51.7% loss of $^{14}$C-oxalate from solution. Both pyrophosphate and citrate showed considerable inhibitory activity of crystal growth at the concentrations studied. Both extract samples caused considerable inhibition, with extract #60 showing the highest inhibitory activity. This experiment demonstrates that the plant extracts cause significant inhibition of calcium oxalate crystal growth in vitro when compared to compounds with known inhibitory activity, i.e., citrate and pyrophosphate.

EXAMPLE 3

Having confirmed that the plant extract inhibited calcium oxalate crystal growth in vitro, an experiment in rats was carried out. The purpose of this experiment was to determine if the extract inhibited kidney stone formation in vivo in an animal model of calcium oxalate stone disease.

When ethylene glycol is ingested by animals or man, 1 to 2 % of the compound is converted to oxalic acid, resulting in dramatic increases in urinary oxalate excretion and deposition of calcium oxalate crystals and stone formation in both kidneys. When 1% ethylene glycol solution was given to rats in the drinking water, the animals developed kidney stones within a period of 21-28 days, (Hodgkinson, A., Oxalic acid in Biology and Medicine. Academic Press, London 1977, p. 251-253). This animal model has proved valuable for many in vivo studies of calcium oxalate stone disease and was used in this experiment.

Male Wistar rats were used in this study. The animals were treated as outlined in Table 2.

TABLE 2

Treatment protocol of rats used to study the effect of the plant extract on prevention and dissolution of calcium oxalate renal stones.

| DAY | III* | IV | V | VI |
|---|---|---|---|---|
| 1-41 | EG | EG | EG + Ex | EG + Ex |
| 42 | EG | Ex | EG + Ex | EG + Ex |
| 47 | EG | Ex HEMATURIA FOR 5 DAYS | EG + Ex | EG + Ex |
| 57 | EG | DIED FROM ANESTHESIA | EG + Ex | EG + Ex |
| 69 | DIED FROM ANESTHESIA | — | EG + Ex | EG + Ex |
| 89 | | | EG + Ex | Ex |
| 97 | | | EG + Ex | Ex HEMATURIA FOR 1 DAY |
| 104 | | | Ex | Ex |

*Data from control Rats I and II omitted for brevity.
EG = ETHYLENE GLYCOL
Ex = EXTRACT Controls, I and II, were given deionized water (i.e., no treatment), III and IV were given 1% (W/V) ethylene glycol (EG) in the drinking water, V and VI were given 1% (W/V) ethylene glycol plus 5% extract, by volume, in the drinking water. All rats received a normal rat chow diet and were housed in individual metabolic cages. All six rats were X-rayed for the presence of renal stones prior to beginning treatment and at intervals thereafter as outlined in Table 3. The results of the X-rays are shown in Table 3.

TABLE 3

Renal stone formation in rats given ethylene glycol (Rats III and VI) or ethylene glycol plus extract (Rats V and VI)

| ANIMALS (RATS) NO. | | III | IV | V | VI |
|---|---|---|---|---|---|
| CONTROL DAY | | N | N | N | N |
| TREATMENT DAY | 14 | N | DEFINITE STONE | N | N |
| | 37 | POSSIBLE STONE | LARGE STONE | N | POSSIBLE SMALL STONE |
| | 57 | DEFINITE LARGE STONE | STONE APPEARED TO BE BREAKING UP. DIED FROM ANESTHESIA | N | DEFINITE SMALL STONE |
| | 69 | LARGE STONE, DIED FROM ANESTHESIA | | N | SMALL STONE |
| | 104 | | | SMALL STONE | STONE SIZE DECREASED |

N = NORMAL = NO STONE
Data for control Rats I and II omitted for brevity.

Animals were fasted for 24 h before each X-ray since the high calcium content of the diet makes interpretation of the X-ray very difficult. Twenty-four hour urine collections were made in a container with 1.0 ml of 7.0 N HCl, added. The control rats I and II (data not shown) were normal throughout the experiment.

Urinary oxalate was determined as described by Costello, J. et al, J. Lab. Clin. Med., 87, 903 (1976). The presence or absence of renal stones was confirmed by a radiologist utilizing X-ray analysis.

Rats I and II (no treatment) did not form renal stones. Rats III and IV formed renal stones by day 57 and 14, respectively, while rats V and VI formed stones by day 104 and 57, respectively. The size of the stones formed by rats III and IV was visibly larger than those formed by rats V and VI.

Rat IV had a very large stone by day 37. On day 42 this animal was taken off EG treatment and given 5% extract in the drinking water. This resulted in severe hematuria (blood in the urine) for 5 consecutive days which is indicative of passage of calcium oxalate crystals in the urine. On X-ray, day 57, the stone appeared to be breaking up, however, the rat died from anesthesia that day. Examination of the kidneys revealed a large number of stones in one kidney. No further analysis on the stone(s) was carried out.

Rat VI had a small renal stone by day 57. On day 69 the extract and EG were discontinued and the animal was given deionized water. On day 89 the rat was given 5% extract which continued until day 140. When both kidneys were removed, dissected and examined for renal stones, no stones could be found.

The results of rat VI are summarized in Table 4.

TABLE 4

The effect of the plant extract on dissolution of a calcium oxalate renal stone in Rat VI.

| Volume (ml/24 h.) | Urine Oxalate (mg/24 h.) | Day of Collection | Comment |
|---|---|---|---|
| 40 | 15.0 | 96 | HEMATURIA |
| 46 | 13.5 | 97 | NO HEMATURIA |
| 45 | 6.3 | 98 | NO HEMATURIA |
| 65 | 8.5 | 99 | NO HEMATURIA |
| 43 | 1.9 | 124 | |

As can be seen on Table 4, this rat excreted very large quantities of oxalate in the urine over the initial period of extract ingestion (days 96–99). Rats on a normal diet excrete 0.5 to 0.7 mg of oxalate per 24 h urine. Postmortem, both kidneys were normal in size and there was no sign of stones in either kidney. Hematuria was observed on day 96 following 5% extract treatment which was restarted on day 89.

This experiment (two rats per group) supports the view that 5% extract has an inhibitory effect on renal stone formation when rats are fed 1% EG compared to animals given 1% EG without extract (rats III and IV). When the presence of renal stones was confirmed, the EG discontinued and the animals (rats IV and VI) treated with extract, there is evidence, especially for rat VI, that the renal stone was disintegrated and passed in the urine as calcium oxalate.

EXAMPLE 4

In the experiment described in Example 3, an inhibitory effect of the extract on renal stone formation as well as causing stone dissolution was observed. The purpose of this experiment was to investigate this inhibitory activity in greater detail in a large group of control and experimental animals. The experimental conditions of fluid intake (i.e., EG intake), weight gain, renal stone formation and calcium oxalate deposition were carefully monitored. Renal function and urinary oxalate excretion were also determined.

The same animal model as described in Example 3 was used. Male Wistar rats were used with 12 animals in each group. Animals were fed ad libitum rat chow diet. Urinary oxalate determination was as described by Costello, J. et al, J. Lab. Clin. Med., 87, 903 (1976).

Animals were housed in individual metabolic cages and allowed 10 days to become acclimated. During this period a 24 h urine was collected and blood withdrawn for determination of urinary oxalate and creatinine clearance values. Twenty-four male Wistar rats were randomly divided into two groups of 12. One group (controls) was given 1% (W/V) ethylene glycol (EG) in the drinking water for 41 days, while the experimental group received 1% (W/V) EG and 10% (V/V) extract in the drinking water for a similar period. Plasma creatinine, BUN, urinary oxalate, creatinine and animal weights were determined prior to beginning treatment. Fluid intake of the animals was carefully recorded daily. Weekly 24 h urinary collections were made for oxalate determination and the urine collected in 3 ml, 3.5 N HCl. BUN and creatinine clearance were also determined at the end of the study. Blood samples were withdrawn by retro-orbital bleeding. After completion of the study the animals were weighed, sacrificed and the kidneys removed for subsequent calcium oxalate analysis.

Kidneys were dissected and visible gross stones removed and weighed. Calcium oxalate crystal deposition refers to deposits that were not visible to the naked eye and consequently had to undergo acid extraction as described hereinbelow. Kidneys were then minced with a scalpel, transferred to screw-top Nalgene centrifuge tubes, lyophilized for 16 h and the dry powder crushed with a spatula. The weight of the wet tissue and lyophilized powder were recorded. Lyophilized kidneys were defatted with four washes of a 1:1 ether: petroleum ether mixture, 2 ml/wash. Washings 1-3 were allowed to settle for 5 min and the organic solvent removed and discarded. Following the final wash, the samples were centrifuged (15 min, 7000 g) to allow maximum removal of the solvent. The tissue was dispersed in each tube and allowed to dry in the fume hood for about 2.5 h before being lyophilized for 1 h.

To extract the calcium oxalate, 6 ml (0.5 N) HCl was added to each tube containing lyophilized defatted kidney tissue. The tubes were capped and continuously mixed for 16 h at room temperature, centrifuged (20 min, 7000 g) and the supernatant removed and retained. A second extraction was carried out using 4 ml (0.5 N) HCl, treated as above and the supernatant combined with the first acid extract in a 50 ml pyrex tube. The volume of the combined supernatants was determined and aliquots retained for calcium determination.

$^{14}$C-oxalate, 100 μl (0.5 μCi/ml) was added to each kidney extract, aliquots (100 μl) removed for counting and the extract titrated to pH 5.0 with NaOH (10 N). Oxalate was precipitated from solution by addition of saturated calcium sulfate and ethanol, 0.33 and 2.25 ml, respectively,/ml acid extract, mixed and allowed to stand at room temperature for 3 h. Tubes were centrifuged (15 min, 1500 rpm), the supernatant removed and discarded and the precipitate lyophilized. The dry precipitate was analyzed as previously described for urinary oxalate, Costello, J. et al, J. Lab. Clin. Med., 87, 903 (1976). Calcium content of the kidney extract was determined by atomic absorption using a Perkin Elmer AA Model 2380. Plasma and urinary creatinine were determined using an Abbot A-Gent creatinine test kit on an Abbot Biochromatic Analyzer 100. Blood urea nitrogen (BUN) was determined using an Abbot A-Gent BUN test kit on the same analyzer.

Results were analyzed using Students t test and p values reported are for a two tail test.

The results are summarized in Table 5. The results are mean ±SD.

TABLE 5

Urinary oxalate excretion, kidney calcium, oxalate, and stone formation, renal function, fluid intake, and weight of rats given ethylene glycol (Controls) or ethylene glycol plus 10% extract (Extract Rats) for 41 days.

| | Control Rats | Rats on Extract | P Value |
|---|---|---|---|
| Urinary oxalate, Prior to treatment (mg/24 h) | 0.656 | 0.574 | N.S. |
| Urinary oxalate during treatment (mg/24 h) | 7.854 ± 3.817 | 4.928 ± 3.023 | <0.001 |
| Kidney calcium (mg/rat) | 2.03 ± 2.806 | 0.237 ± 0.117 | <0.05 |
| Kidney oxalate (mg/rat) | 4.59 ± 5.627 | 0.227 ± 0.189 | <0.02 |
| mg of stones formed/group | 11.4 | 4.1 | N.S. |
| Number of stones formed/group | 54 | 21 | N.S. |
| *Total kidney calcium oxalate (mg/rat) | 7.570 ± 8.882 | 0.805 ± 1.098 | <0.02 |
| Rat weight before study (gr/rat) | 201.6 ± 30.9 | 193.5 ± 26.4 | N.S. |
| Rat weight at end of study (gr/rat) | 337.8 ± 30.6 | 327.3 ± 41.3 | N.S. |
| Fluid intake/rat, during study (ml/24 h) | 41.8 ± 4.9 | 38.9 ± 8.5 | N.S. |
| Creatinine clearance before study (ml/min) | 0.86 ± 0.48 | 0.93 ± 0.29 | N.S. |
| Creatinine clearance at end of study (ml/min) | 1.15 ± 0.42 | 1.70 ± 0.23 | <0.001 |

All the above values are mean ± SD.
There were 12 rats in each group.
*The sum of kidney stones (mg) and calcium oxalate deposits, mg/rat.
**The p values, Table 5, reported are for a two tail test, and are derived by comparing each column in the control group with the corresponding column in the extract-treated group.

TABLE 6

Calcium and Oxalic Acid Content of Each Kidney (A and B) of Control Rats

| | Calcium | | Oxalic Acid | |
|---|---|---|---|---|
| | (A) | (B) | (A) | (B) |
| Rat # | mg | | mg | |
| 1 | 0.149 | 0.094 | 0.225 | 0.527 |
| 2 | 0.089 | 0.062 | 0.516 | 0.250 |
| 3 | 0.149 | 0.157 | 0.118 | 0.279 |
| 4 | 0.137 | 0.086 | 0.292 | 0.372 |
| 5 | 3.899 | 4.736 | 8.517 | 9.660 |
| 6 | 0.312 | 0.385 | 1.022 | 2.366 |
| 7 | 2.209 | 2.172 | 4.676 | 4.466 |
| 8 | 3.266 | 2.889 | 6.237 | 6.012 |
| 9 | 0.409 | 0.317 | 0.840 | 2.056 |
| 10 | 0.914 | 0.423 | 1.531 | 1.300 |
| 11 | 0.156 | 0.196 | 0.284 | 1.260 |
| 12 | 0.344 | 0.826 | 0.704 | 1.602 |

TABLE 7

Calcium and Oxalic Acid Content of Each Kidney (A and B) of Rats on Extract

| | Calcium | | Oxalic Acid | |
|---|---|---|---|---|
| | (A) | (B) | (A) | (B) |
| Rat # | mg | | mg | |
| 1 | 0.176 | 0.141 | 0.235 | 0.119 |
| 2 | 0.135 | 0.091 | 0.158 | 0.063 |
| 3 | 0.172 | 0.139 | 0.208 | 0.106 |
| 4 | 0.126 | 0.120 | 0.140 | 0.082 |
| 5 | 0.070 | 0.092 | 0.048 | 0.044 |
| 6 | 0.082 | 0.088 | 0.049 | 0.029 |
| 7 | 0.089 | 0.061 | 0.086 | 0.040 |
| 8 | 0.249 | 0.287 | 0.385 | 0.331 |

TABLE 7-continued

Calcium and Oxalic Acid Content of
Each Kidney (A and B) of Rats on Extract

| Rat # | Calcium (A) mg | Calcium (B) mg | Oxalic Acid (A) mg | Oxalic Acid (B) mg |
|---|---|---|---|---|
| 9 | 0.071 | 0.071 | 0.082 | 0.026 |
| 10 | 0.158 | 0.145 | 0.191 | 0.156 |
| 11 | 0.062 | 0.087 | 0.027 | 0.007 |
| 12 | 0.062 | 0.070 | 0.061 | 0.042 |

TABLE 8

Weekly Urinary Oxalate excretion in male Wistar rats on
1% Ethylene Glycol in drinking water for 41 days (mg/24 h)

| Week | 1 | 2 | 3 | 4 | 5 |
|---|---|---|---|---|---|
| Rat 1 | 5.124 | 7.438 | 6.809 | 3.452 | 2.957 |
| 2 | 4.578 | 7.422 | 10.209 | 7.621 | 7.470 |
| 3 | 1.844 | 6.376 | 6.649 | 6.777 | 10.814 |
| 4 | 5.093 | 5.774 | 3.984 | 4.765 | 8.592 |
| 5 | 7.039 | 8.239 | 6.220 | 7.870 | 11.731 |
| 6 | 8.275 | 10.161 | 7.080 | 7.473 | 10.355 |
| 7 | 5.4057 | 5.274 | 5.112 | 9.665 | 15.798 |
| 8 | 7.910 | 4.491 | 4.801 | 3.123 | 11.674 |
| 9 | 8.107 | 5.247 | 6.429 | 9.811 | 11.904 |
| 10 | 1.074 | 7.057 | 11.495 | 11.206 | 14.245 |
| 11 | 2.519 | 1.745 | 6.577 | 6.691 | 8.625 |
| 12 | 10.657 | 9.552 | 14.906 | 14.674 | 17.253 |
| mean | 5.635 | 6.565 | 7.523 | 7.761 | 10.952 |
| ± SD | 2.89 | 2.30 | 3.14 | 3.29 | 3.85 |

TABLE 9

Weekly Urinary Oxalate excretion in male Wistar rats
on 1% Ethylene Glycol and 10% extract in drinking water
for 41 days (mg/24 h)

| Week | 1 | 2 | 3 | 4 | 5 |
|---|---|---|---|---|---|
| Rat 1 | 3.984 | 3.289 | 6.262 | 9.969 | 9.773 |
| 2 | 3.828 | 4.255 | 4.921 | 1.646 | 3.794 |
| 3 | 9.818 | 9.498 | 8.035 | 8.178 | 9.086 |
| 4 | 4.604 | 6.470 | 6.603 | 4.052 | 9.710 |
| 5 | 1.204 | 2.502 | 6.552 | 5.905 | 12.204 |
| 6 | 2.419 | 3.762 | 6.616 | 7.077 | 6.679 |
| 7 | 1.129 | 5.176 | no sample | 4.225 | 5.192 |
| 8 | 3.247 | 4.680 | 4.582 | 8.759 | 11.517 |
| 9 | 3.530 | 5.984 | 6.475 | 2.270 | 6.329 |
| 10 | 6.847 | 3.570 | 3.358 | 2.772 | 3.092 |
| 11 | 0.701 | 4.523 | 2.466 | 3.610 | 3.557 |
| 12 | 0.887 | 1.944 | 1.779 | 2.088 | 1.677 |
| mean | 3.517 | 4.638 | 5.241 | 5.046 | 6.884 |
| ± SD | 2.69 | 2.02 | 1.99 | 2.85 | 3.52 |

TABLE 10

Comparison of Total Kidney Calcium Oxalate Deposits
(Renal Stones Plus Calcium Oxalate Crystal Deposition)
In Control Rats (1% Ethylene Glycol) and Extract-Treated
Rats (1% Ethylene Glycol Plus 10% Extract)

| Control Rat No. | Renal Stones mg/Rat | Kidney Calcium Oxalate Deposits mg/rat | *Total Kidney Calcium Oxalate mg/Rat |
|---|---|---|---|
| Controls | | | |
| 1 | 0 | 0.995 | 0.995 |
| 2 | 0 | 0.910 | 0.910 |
| 3 | 0 | 0.703 | 0.703 |
| 4 | 0 | 0.887 | 0.887 |
| 5 | 0.1 | 26.812 | 26.912 |
| 6 | 0.5 | 4.085 | 4.585 |
| 7 | 1.9 | 13.523 | 15.423 |
| 8 | 3.2 | 18.404 | 21.604 |
| 9 | 1.9 | 3.586 | 5.486 |
| 10 | 3.1 | 4.168 | 7.268 |
| 11 | 0.4 | 1.896 | 2.296 |
| 12 | 0.3 | 3.476 | 3.776 |
| Extract-Treated | | | |
| 1 | 0.6 | 0.671 | 1.271 |
| 2 | 0.1 | 0.447 | 0.547 |
| 3 | 0.2 | 0.625 | 0.825 |
| 4 | 0 | 0.468 | 0.468 |
| 5 | 0 | 0.254 | 0.254 |
| 6 | 0 | 0.248 | 0.248 |
| 7 | 0.2 | 0.276 | 0.476 |
| 8 | 2.9 | 1.252 | 4.152 |
| 9 | 0.1 | 0.250 | 0.350 |
| 10 | 0 | 0.650 | 0.650 |
| 11 | 0 | 0.183 | 0.183 |
| 12 | 0 | 0.235 | 0.235 |
| **p | NS | 0.02 | 0.02 |

*Total kidney calcium oxalate (column 4) is the sum of renal stones (column 2) and calcium oxalate deposits (column 3) in mg per rat.

There was a substantial increase in urinary oxalate excretion of both groups during EG ingestion, however, control rats excreted significantly more oxalate ($p < 0.001$) than rats on extract, Table 5 (also Tables 7 and 8). These results suggest the extract may inhibit oxalate synthesis from EG in this animal model. The number and weight of renal stones found in the control rats were greater than in the experimental group but neither reached significance, Table 5. Kidney calcium in the control rats was almost 9 times that found in the extract treated rats ($p < 0.05$), while the oxalate content was 20 times higher in the control rats, ($p < 0.02$) Table 5. These results demonstrate substantial inhibition of renal calcium oxalate crystal deposition in the extract treated group. If the weight (in mg) of renal stones found in each animal (and presumed here to be calcium oxalate, although not analyzed) is combined with the weight of calcium oxalate deposits, the total calcium oxalate deposition (i.e., weight in mg of renal stones plus acid extracted calcium oxalate deposits) in the control group is significantly more than that in the experimental group $p < 0.02$, Table 5.

Recent in vivo observations (Kok, D. J. et al, Crystal agglomeration is a major element in calcium oxalate urinary stone formation. Kidney Int., 37, 51, 1990) while identifying crystal growth as an important part in the process of stone formation, suggest that crystal agglomeration is the decisive element in the formation of large crystal particles and therefore in the process of renal stone formation. Since the extract significantly inhibits crystal deposition/stone formation in rats fed 1% EG, it is reasonable to suggest that it inhibits not only crystal growth, as shown by in vitro studies, but also inhibits crystal agglomeration (formation of crystal clumps) in vivo.

The BUN value of the control rats was significantly higher ($p < 0.05$, data not shown) than the extract group while their renal function, as determined by creatinine clearance, 1.15 ml/min was significantly less than the extract treated rats, Table 5. These findings demonstrate that the extract prevented loss of renal function probably as a result of decreased renal calcium oxalate crystal deposition in this group. By comparison, the control rats showed significant loss of renal function.

The water intake and weight of the rats are shown in Table 5, and no significant difference in either parameter was observed. The significant difference in calcium oxalate deposition and renal function between the two groups, Table 5 and discussed above, cannot therefore be accounted for by differences in intake of EG.

In Tables 6 and 7 the individual calcium and oxalate content of both kidneys from each rat are provided, while in Tables 8 and 9 the weekly urinary oxalate values of each animal over five consecutive weeks as well as weekly mean values for each group of animals are shown.

The results can be summarized as follows:
1. Extract treated rats excreted significantly less oxalate in the urine, suggesting inhibition of oxalate synthesis from EG.
2. Kidney calcium and oxalate were significantly lower in the extract group demonstrating inhibition of calcium oxalate deposition by the extract.
3. Kidney function was significantly greater in the extract group at the completion of the study, again supporting the view that the extract inhibits calcium oxalate crystal deposition and loss of renal function.
4. Number and weight of renal stones was greater in the control group but did not reach significance.
5. However, when the weight of renal stones (presumed to be calcium oxalate) in each rat is combined with the weight of calcium oxalate crystal deposits, control rats have significantly more total calcium oxalate deposited in their kidneys than the extract group.
6. It is suggested from these findings that the extract prevents calcium oxalate crystal formation in vivo.
7. Fluid intake and therefore EG intake was similar in both groups.
8. Weight gain was similar in both groups over the period of the study.

In the above experimental renal stone animal model the extract showed potent inhibitory activity in preventing calcium oxalate crystal deposition and loss of renal function. The significant decrease in urinary oxalate excretion in the presence of extract ingestion suggests inhibition of oxalate synthesis from EG.

EXAMPLE 5

The purpose of this investigation was to determine the effect, if any, of extract ingestion on EG absorption from the gut (gastrointestinal tract). It was important to determine any change in absorption of EG due to extract ingestion, in order to establish more clearly the site of action of the extract on renal calcium oxalate stone formation.

Male Wistar rats were housed and fed as described in Example 3. Tracer $^{14}$C-EG (4.7 mCi/mmol) in an amount of 1.6 $\mu$Ci/rat/day was added to the drinking water to monitor absorption of EG. The urinary $^{14}$C values and fecal loss of $^{14}$C label as an indication of gastrointestinal absorption were determined.

Twenty-four hour fecal collection was mixed with HCl (25%), 1.0 ml/0.1gr feces, allowed to extract for 3h at room temperature, and then centrifuged (15 min, 1500 rpm). The supernatant was decanted, volume determined and 0.5 ml aliquots taken for scintillation counting in Biofluor scintillation fluid on a Packard liquid scintillation counter. The dpm were determined by quench correction.

$^{14}$C present in urine was similarly determined by counting 0.5 ml of a 24-h urine collection. The daily intake of $^{14}$C-EG was determined by monitoring the water intake and counting an aliquot of the drinking water as described above for urine.

Twelve male Wistar rats were acclimated in individual metabolic cages for one week. Animals were then randomized into two groups, 6 rats/group, control and experimental. Control animals received 1% (W/V) EG and $^{14}$C-EG (1.6 $\mu$Ci/rat/day) in the drinking water, while the experimental group received 1% (W/V) EG and $^{14}$C-EG, as in controls, and 10% extract (by volume). Both groups were studied over 5 consecutive days. Daily 24-h urine and fecal collections were made throughout the study and the intake of drinking solution accurately recorded per 24-h period.

The fecal and urinary $^{14}$C excretion values are shown in Table 11.

TABLE 11

Urinary and fecal excretion of $^{14}$C in control rats and rats on extract (10% by vol) following oral ingestion or $^{14}$C-ethylene glycol.

|  | Rats on Extract | | Control Rats | |
|---|---|---|---|---|
|  | urine | feces | urine | feces |
| DAY 1 | 36.8 ± 4.2 | 1.94 ± 0.62 | 31.2 ± 3.8 | 0.65 ± 0.33 |
| 2 | 48.2 ± 6.4 | 2.28 ± 1.14 | 38.1 ± 4.3 | 2.45 ± 1.30 |
| 3 | 44.3 ± 9.9 | — | 40.9 ± 7.16 | — |
| 4 | 40.9 ± 9.1 | — | 38.0 ± 3.04 | — |
| 5 | 39.2 ± 4.3 | 1.39 ± 0.4 | 35.9 ± 4.12 | 1.47 ± 1.15 |
| P | N.S. | | | |

Results are expressed as a percentage of the $^{14}$C-EG intake (% dpm) and mean ±S shown for each group. Fecal $^{14}$C-excretion for days 3 and 4 are not shown as these samples were lost. Urinary $^{14}$C-excretion was similar in both groups, except for day 2 when the extract-treated rats showed a significantly greater excretion, p <0.01. However, when compared over the 5-day period, there was no significant difference between the groups. Fecal $^{14}$C was higher in the extract group on day 1, and similar on days 4 and 5, but was only a small percentage of the total $^{14}$C ingested on each day. The results show that 10% extract solution does not significantly alter the absorption of 1% EG.

From the above, it can be concluded that the inhibitory effect of the extract on renal calcium oxalate deposition demonstrated in the previous study does not result from altered EG absorption. The findings support the view that the extract prevents calcium oxalate deposition by acting at a renal site.

EXAMPLE 6

Treatment of Plant Extract with Heptane, Hexane, and Chloroform Methanol

An aqueous solution of an extract was treated separately with equal volumes of hexane and heptane, vortexed vigorously for 1.5 min, centrifuged at 1,000 rpm for 10 minutes, and the lower aqueous phase removed for assay. Two ml of extract was also treated with 4 ml of a mixture of chloroform/methanol (1:1 V/V), vortexed and centrifuged as above, and the upper aqueous-methanol phase retained for assay. All samples were assayed in duplicate and compared to the untreated extract. Five $\mu$l of all samples were assayed except the chloroform/methanol-treated sample in which 10 $\mu$l was used to correct for a 1:2 dilution by the methanol.

| Sample | Results<br>% Inhibition of Crystal Growth |
|---|---|
| Untreated extract | 44.20 |
| Hexane-treated | 50.53 |
| Heptane-treated | 46.22 |
| Chloroform/Methanol-treated | 42.63 |

These data show that there is no significant loss of activity when the extract is treated with hexane, heptane or chloroform/methanol, demonstrating that all the activity remains in the aqueous phase and is not soluble in these organic solvents.

EXAMPLE 7

Solubility of Inhiitor Activity in Diethyl Ether

Four ml of aqueous extract, N-3, was treated with 40 ml of ether and mixed by vigorous stirring for 20 min and the aqueous phase removed by a separating funnel. The aqueous phase was further mixed with 10 ml of ether for 5 min and again separated. The ether phase from both extractions was combined, allowed to evaporate, lyophilized and redissolved in 0.5 ml of distilled water. The treated extract (aqueous phase) showed no loss in activity while the ether extract contained no more than 2% of the total inhibitory activity.

EXAMPLE 8

Treatment of Extract with Ethanol

When 2.5 ml of ethanol (200 proof) was added to 1.0 ml of extract N-3 an immediate precipitate formed. The sample was centrifuged, supernatant removed, and the precipitate redissolved in 3.5 ml of distilled water. The resuspended precipitate contained over 85% of the inhibitory activity of N-3.

EXAMPLE 9

Typical Purification of Inhibitor of Crystal Growth from Plant Extract

A frozen liquid plant extract was prepared from the leaves in a similar fashion to that described in Example 1, and was then stored at −20° C. The frozen liquid extract was thawed out in hot water, 5 ml removed, mixed with 5 ml of hexane, vortexed for about 2 minutes, centrifuged for 10 minutes at 1,000 rpm, and the lower phase, approximately 4.6 ml, removed and lyophilized. The dry powder (about 40 mg) was dissolved in 2.0 ml of Tris-HCl, 0.02 M, pH 7.38, and chromatographed on a G-75 Sephadex column (dimensions 1×44 cm) which was equilibrated with the same Tris-HCl buffer. The sample was eluted from the column at a flow rate of 40 ml/h, and 144, 1.0 ml fractions collected and assayed for activity. The active peak (fractions containing most inhibitory activity of calcium oxalate crystal growth) was eluted in fractions, 13–32, which were combined, dialyzed against distilled water through a membrane with a molecular weight cut off of 12,000–14,000 daltons, and then lyophilized. The powder was redissolved in 4.5 ml of distilled water, and further purified by isoelectric focusing on a BioRad Rotofor (conditions: 1% ampholytes, 653 volts, 19 mA, 12 watts for 70 minutes). Fractions 1-3, which had most of the activity, were combined, dialyzed as above, and lyophilized. The lyophilized extract was a white powder. The activity of this purified powder was 183,871 U/gr compared to 17,400 U/gr for the unpurified extract.

In future studies, the above purification will be somewhat modified in preparing larger quantities of purified inhibitor. Following elution of the active peak fractions from G-75 Sephadex and dialysis, the samples will be chromatographed on a DEAE Sephadex-A25 (2.5×20 cm) column, and eluted with a linear NaCl gradient, 0–2.0 M. This step should concentrate the sample and result in further purification. Following this ion exchange step, the activity will be precipitated with ethanol, redissolved in distilled water and run on isoelectric focusing as described in Example 12 below, again treated with ethanol as above, and lyophilized. The purity of the extract will be further examined by running on an appropriate HPLC column.

EXAMPLE 10

Effect of pH adjustment on inhibitory activity of extract N-1

Effect of acidic pH

A 5 ml aliquot of extract N-1, pH 5.33, was titrated to pH 1.48 with 1N HCl, left to stand at 4° C for 14 h, and then titrated to pH 5.36 (close to original pH) with 1N NaOH. The acid-treated sample showed no loss in activity compared to the control untreated extract.

| Extract Sample | % Inhibitory Activity* |
|---|---|
| N-1 (untreated)** | 37.32 |
| N-1 (pH adjusted) | 37.47 |

*Inhibitory activity against calcium oxalate crystal growth.
**Value corrected for dilution effect of N-1 with acid/alkali.

EXAMPLE 11

Effect of alkaline pH

Aliquots of extracts, N-1, N-2, and #-60, were titrated to pH 12.60 or slightly higher with 2.5 N NaOH, left to stand for a minimum of 15 h at 4° C, and then titrated to within 0.1 of original pH with 3.5 N HCl. All samples were assayed for activity along with untreated controls. All three extracts showed a substantial increase in activity against calcium oxalate crystal growth as shown below.

| Extract # | % Inhibitory Activity | | |
|---|---|---|---|
| | Untreated* | pH Adjusted | |
| | | (undiluted) | (1:6 diluted) |
| N-1 | 35.1 | 80.3 | 36.0 |
| N-2 | 34.0 | 74.7 | 23.6 |
| #-60 | 38.4 | 72.7 | 20.2 |

*These values, Example 11, were corrected for dilution effect resulting from acid/alkali addition to the treated extract.

A similar increase in activity was obtained when N-1, pH 12.7, was put in a boiling water bath for 1 h and the pH then adjusted to near original value (data not shown). When purified N-1 (hexane-treated 1:1, chromatographed on G-75 Sephadex, active fractions combined, dialyzed, and lyophilized) was treated in a similar way, activity increased from 22.6% to 49.4%. Since the large increase in activity is not reversed on titration back to the original pH, and occurs to both the unpurified and purified extracts it suggests a permanent modification to the inhibitor or other active ingredient(s)

present in the extract. The increase may be a consequence of a chemical or structural alteration to the inhibitory active ingredient(s) or the conversion of an inactive ingredient ("pre-inhibitor") to an active ingredient (inhibitor).

Stability of purified extract and modified extract (pH adjusted

N-2 which had been adjusted to pH 12.6 for 16 h and then readjusted to original pH (i.e., modified N-2) was put in a boiling bath for 3 h. A separate aliquot of N-2 was adjusted to pH 1.5 for 16.5 h. Both treatments of N-2 caused little or no loss in activity. Purified N-1 (Sephadex G 100/120, dialyzed and lyophilized) showed no loss in activity when kept at pH 12.7 for 16.5 h, pH 1.5 for 16.5 h, and when boiled for 3 h (data for these experiments not shown). The results confirm that these different preparations of the extract show no loss in activity when treated with acid, alkali, or heat. (The increase in activity following alkali treatment is discussed in Example 11.)

EXAMPLE 13

Isoelectric point (pI) determination of plant extract inhibitor of calcium oxalate crystal growth Extract samples were run on a BioRad isoelectric focusing cell that allows collection of the different "pH fractions" in separate test tubes at the end of the run.

Isoelectric point (pI) of extact inhibitor

The following samples were focused on the Rotofor cell(Bio-Rad free solution isoelectric focusing apparatus), purified N-1 (Sephadex G-100/120, dialyzed, lyophilized), N-3, purified N-1 (dialyzed, EDTA/EGTA treated, run on G-75, peak fractions focused), modified N-1 (pH 12.7 for 16 hr, titrated to original pH). All samples were focused following two pre-focusing steps (a) and (b):

(a) 3 M urea containing 0.75% ampholytes was focused for 60–75 min.

(b) Following step (a), 5–7 ml was removed from position one and replaced with 5 ml of 0.2 M phosphoric acid and the cell focused again. Following steps (a) and (b) about 5 ml was removed from position 10, the appropriate sample to be focused was added to position 10, and the cell focused again. After this third and final run, all 20 fractions were harvested, and both the pH and activity were determined. Similar pI values were obtained for all samples, giving a mean pI value of 3.07.

It has been observed by Gelsema et al, Journal of Chromatography, 171:171–181 (1979), that the apparent pI (pI app) in the presence of 3M urea, used in the present studies described above, is greater than the pI by 0.3 of a pH unit (i.e., pI app - pI =0.3). Consequently, a correction of 0.3 to the value derived above would give a pI of approximately 2.7±0.5 (SD).

EXAMPLE 14

Binding of an inhibitor of crystal growth from extract N-2 to calcium oxalate crystals.

Calcium oxalate crystals were generated in the presence of 50 ml of extract N-2 by the simultaneous dropwise addition of 25 ml of 0.2 M solutions of $CaCl_2$ and potassium oxalate over 1 h at 45°–50° C. Stirring was continued for a further 2h and the suspension centrifuged at 2,500 rpm for 10 min, supernatant removed (96 ml), and the precipitate washed with 15 ml distilled $H_2O$, centrifuged as above and the supernatant removed.

To the crystal pellet was added 30 ml of 0.9% NaCl in 3.5 N HCl and mixed; few crystals dissolved. Four grams of KCl was then added to the crystal suspension and shaken for approximately 2h, and the suspension dialyzed against 2 l of 1 M KCl for 17 h at 22° C. through a dialysis membrane with a molecular weight cut off of 12,000–14,000 daltons. The suspension was recovered and centrifuged, 1500 rpm for 15 min, and the supernatant, 32 ml, removed and retained. The supernatant was further dialyzed against 5 l distilled $H_2O$ at pH 2.0 for 67 h, against 5 l $H_2O$ for 24 h, and, finally, against 4 l $H_2O$ for 25 h. The dialyzed solution, 29.5 ml, was lyophilized to give 12.7 mg of white powder. Analysis of the recovered powder confirmed it had considerable inhibitory activity (57,834 U/g) and that the inhibitor was strongly adsorbed onto calcium oxalate crystals.

EXAMPLE 15

Binding of calcium and magnesium by the extract:

N-1 extract was dialyzed in Spectra Port 6 dialysis tubing (MW cut off 10,0000) against deionized water over 6 days with several changes of deionized water. Little or no inhibitory activity was lost. Aliquots of N-1 post dialysis were separately mixed with EDTA 100mM, EGTA 3mM, and EDTA 100mM +EGTA 3mM, final concentrations. Samples were then redialyzed through Spectra Por 2 against deionized water. The results below show that calcium and magnesium bind to the extract fraction containing the inhibitory activity. Magnesium is more readily removed following treatment with EDTA than is calcium. All the calcium could not be removed. EGTA was less effective than EDTA in removing calcium (data not shown). These results confirm that calcium is bound to the extract fraction containing the inhibitory activity along with magnesium but calcium is more firmly bound.

| Results Effect of Dialysis, and treatment with EDTA and EGTA on Calcium and Magnesium Concentrations of N-1 | | |
|---|---|---|
| | Calcium | Magnesium |
| | (mg/100 ml) | |
| Original extract N-1 | 8.78 | 7.74 |
| After exhaustive dialysis against deionized water | 1.03 | 0.73 |
| Mixed with 100 mM EDTA and then dialyzed | 0.049 | 0.008 |
| Mixed with 3 mM EGTA + 100 mM EDTA and then dialyzed | 0.084 | 0.010 |

EXAMPLE 16

Confirmation of a Polyanion

The presence of polyanions in extract N-3 was determined with Alcian Blue 8 GX(Sigma) as described by Fellstrom at al (European J. Clinical Investigation 16, 292, 1986). Heparin was used as a standard. The inhibitory activity was precipitated from N-3 with 2.5 volumes of ethanol (as described in Example 8) and the lyophilized precipitate redissolved in distilled water and assayed for polyanions. The assay confirmed the presence of a considerable quantity of polyanions (>45%) in the fraction of N-3 precipitated with ethanol. This fraction also contained over 85% of the inhibitory activity of N-3 suggesting that the inhibitory ingredient is a polyanion (data not shown).

EXAMPLE 17

Chemical Composition of Extract Inhibitor

Aliquots of N-3 and purified N-1 (Sephadex G100/120, dialysis and lyophilization) were analyzed for the presence of (a) carbohydrate, (b) protein, and (c) ribonucleic acid.

Anthrone test for carbohydrate (qualitative): Aliquots of N-3 and purified N-1 (Sephadex G100/120, dialyzed, lyophilized) were assayed for carbohydrate. To 2 ml of Anthrone reagent (0.2%, W/V, Anthrone in concentracted sulfuric acid) in a test tube, 200 ul of sample was added. Both N-3 and purified N-1 formed a green color which is positive for carbohydrate.

Bio-Rad (Comassie Blue) protein assay: Aliquots of N-3, precipitate of N-3 (precipitated with ethanol and NaCl and redissolved in distilled water), and purified N-1 (G100/120, dialyzed, lyophilized), were assayed for protein. Bovine serum albumin was used as a standard. There was no protein detectable in any of the samples, N-3, precipitate of N-3, or purified N-1.

Pronase test for presence of protein in extract inhibitor: Aliquots of N-3 and purified N-1, as above, were incubated with Pronase (a non-specific protease from Streptomyces griseus) for 24 h as described by Koide et al. (Invest Urol 18, 382, 1981) with appropriate controls. Results show a loss of 20% of the inhibitory activity from purified N-1 preparation, but no loss from N-3 extract. These contradictory results suggest that the inhibitory ingredient may contain a protein/peptide component.

Ribonuclease assay for presence of ribonucleic acid: If the inhibitor is composed of ribonucleic acid, treatment with the enzyme, ribonuclease, should destroy its activity. Aliquots of N-3 and purified N-1, as above, were incubated with ribonuclease for 24 h as described by Koide et al. (Invest Urol 18, 382, 1981). Controls containing N-3 and N-1 without ribonuclease, as well as, ribonuclease only in buffer were also run. Results show no loss of inhibitory activity after ribonuclease treatment and suggest the inhibitory ingredient(s) not to be ribonucleic acid.

Assay for the presence of uronic acids in extract inhibitor: Aliquots of N-3 and precipitate of N-3 (precipitated with ethanol and NaCl and redissolved in distilled water) were assayed for uronic acid content as described by Blumenkrantz and Asboe-Hansen (Anal Biochem 54, 484, 1973). Glucuronic acid as a standard. Results show that N-3 contains $2.6 \pm 0.1$ (SD) mg uronic acid/ml and the ethanol precipitate of N-3 $4.3 \pm 0.2$ (SD) mg/ml or $4.3 \pm 0.2$ mg/14 mg (i.e., 29% is uronic acid). Since the ethanol precipitate also contains >85% of the inhibitory activity of N-3 (see Example 8) the results suggest the inhibitor contains a high percentage of uronic acid. Based on these results there is a high probability that the inhibitor is a glycosaminoglycan type substrate.

A summary of the above results suggest the extract inhibitor does not contain ribonucleic acid but contains carbohydrate, and may be a glycosaminoglycan. The protein analyses suggest it is not a protein, but does not exclude the possibility that it may contain a protein/peptide component.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A purified composition having the following properties:
   inhibits calcium oxalate crystal growth in vitro;
   inhibits renal calcium oxalate crystal deposition in rats which are fed 1% ethylene glycol;
   is anionic and binds to anion exchange resin DEAE-A25 at pH 8.6;
   is soluble in water;
   is stable when heated in an aqueous solution (at pH of extract) at 98° C. for at least three hours;
   retains activity when exposed to an aqueous solution of pH 1.5 for 14 hours;
   retains or shows increased activity when exposed to an aqueous solution of pH 12.7 for 15 hours; and
   has a purity level of at least 50,000 Units of activity per gram of solid matter.

2. The purified composition of claim 1, which has the following additional property:
   binds to calcium oxalate crystals.

3. The composition of claim 1, which is prepared by extracting the composition from the cells of the plant *Eriobotrya japonica*.

4. The composition of claim 1, which is prepared by extracting the composition from cells of the plant *Eriobotrya japonica* and treating the composition at a basic pH to increase the activity of the composition.

5. The purified composition of claim 1, which has a purity of at least about 150,000 Units of activity per gram of solid matter.

6. A purified extract which is extracted from cells of the plant *Eriobotrya japonica*, said extract having the following properties:
   inhibits calcium oxalate crystal growth in vitro;
   inhibits renal calcium oxalate crystal deposition in rats which are fed ethylene glycol;
   retains activity when exposed to an aqueous solution of pH 1.5 to 14 hours;
   shows increased activity when exposed to an aqueous solution of pH 12.7 for 15 hours;
   is stable when heated in an aqueous solution (at pH of extract) at 98° C. for 3 hours;
   is soluble in water;
   is insoluble in heptane, hexane, chloroform/methanol mix, and diethyl ether;
   is precipitated from an aqueous solution by ethanol;
   binds to DEAE-A-25 Sephadex at pH 8.6 and is eluted from said DEAE-A-25 Sephadex with 2 M NaCl; and
   has a purity level of at least 50,000 Units of activity per gram of solid matter.

7. An extract from cells of the plant *Eriobotrya japonica* which has been treated at a pH above 12, said extract having the following properties:
   inhibits calcium oxalate crystal growth in vitro;
   inhibits renal calcium oxalate crystal deposition in rats which are fed ethylene glycol;
   retains activity when exposed to an aqueous solution of pH 1.5 for 14 hours;
   is stable when heated in an aqueous solution (at pH of extract) at 98° C. for 3 hours;
   is soluble in water; and
   binds to DEAE-A-25 Sephadex at pH 8.6.

8. A pharmaceutical composition suitable for the treatment of calcium oxalate stone disease, comprising:
an effective amount of the composition of claim 1; and
a pharmaceutically acceptable carrier therefor.

9. The pharmaceutical composition of claim 8, in a form suitable for oral administration.

10. The pharmaceutical composition of claim 8, in a form suitable for parenteral administration.

11. A purified material which is prepared by extracting the material from cells of the plant *Eriobotrya japonica*, said purified material having the following properties:
inhibits calcium oxalate crystal growth in vitro;
inhibits renal calcium oxalate crystal deposition in rats which are fed 1% ethylene glycol;
is anionic and binds to anion exchange resin DEAE-A-25 at pH 8.6;
is soluble in water;
is stable when heated in an aqueous solution (at pH of extract) at 98° C. for at least three hours;
retains activity when exposed to an aqueous solution of pH 1.5 for 14 hours;
retains or shows increased activity when exposed to an aqueous solution of pH 12.7 for 15 hours; and
has a purity level of at least 50,000 Units of activity per gram of solid mater.

12. A method for treating calcium oxalate stone disease, comprising: administering to a patient who has been diagnosed as having a propensity to develop calcium oxalate stones an effective amount of the composition of claim 1.

13. The method of claim 12, wherein said composition is administered to a patient who is diagnosed as having stones at the time of administration.

14. The method of claim 12, wherein said composition is administered for at least one month to a patient who has a propensity to develop stones.

15. The method of claim 12, wherein said composition is administered to a patient who has suffered from stone disease and wherein the composition is administered at least three times a week for at least three months to prevent or reduce recurrence of stone disease.

16. A method for inhibiting the growth of calcium oxalate crystals which comprises adding the composition of claim 1 to a solution containing calcium and oxalic acid with or without calcium oxalate crystals.

17. A method for treating calcium oxalate stone disease, comprising: administering to a patient who has been diagnosed as having a propensity to develop calcium oxalate stones an effective amount of the extract of claim 6.

18. A method for treating calcium oxalate stone disease, comprising: administering to a patient who has been diagnosed as having a propensity to develop calcium oxalate stones an effective amount of the extract of claim 7.

19. A method for treating calcium oxalate stone disease, comprising: administering to a patient who has been diagnosed as having a propensity to develop calcium oxalate stones an effective amount of the extract of claim 11.

* * * * *